US010485552B1

(12) United States Patent
Makhoul

(10) Patent No.: US 10,485,552 B1
(45) Date of Patent: Nov. 26, 2019

(54) APPARATUS AND METHOD FOR CONTROLLING SYSTEMIC BLOOD PRESSURE IN PATIENTS

(71) Applicant: Imad R. Makhoul, Akko (IL)

(72) Inventor: Imad R. Makhoul, Akko (IL)

( * ) Notice: Subject to any disclaimer, the term of this patent is extended or adjusted under 35 U.S.C. 154(b) by 0 days.

(21) Appl. No.: 16/234,680

(22) Filed: Dec. 28, 2018

(51) Int. Cl.
| *A61B 17/135* | (2006.01) |
| *A61B 5/03* | (2006.01) |
| *A61B 5/022* | (2006.01) |
| *A61B 17/00* | (2006.01) |

(52) U.S. Cl.
CPC ...... *A61B 17/1355* (2013.01); *A61B 5/02241* (2013.01); *A61B 5/031* (2013.01); *A61B 2017/00022* (2013.01); *A61B 2503/045* (2013.01)

(58) Field of Classification Search
CPC . A61B 17/1355; A61B 5/031; A61B 5/02241; A61B 2017/00022; A61B 2503/045
See application file for complete search history.

(56) References Cited

U.S. PATENT DOCUMENTS

| 5,103,828 | A | 4/1992 | Sramek |
| 2004/0111006 | A1 | 6/2004 | Alferness et al. |
| 2004/0147956 | A1 | 7/2004 | Hovanes et al. |
| 2009/0287069 | A1 | 11/2009 | Naghavi et al. |
| 2011/0190807 | A1* | 8/2011 | Redington ......... A61B 17/1355 606/201 |
| 2011/0238107 | A1* | 9/2011 | Raheman ............... A61B 5/412 606/202 |
| 2014/0024986 | A1 | 1/2014 | Souma |
| 2015/0094755 | A1 | 4/2015 | Hong |
| 2015/0190301 | A1* | 7/2015 | Leschinsky ........ A61B 5/02208 601/149 |
| 2015/0265286 | A1 | 9/2015 | Raheman |
| 2015/0359440 | A1* | 12/2015 | Kvernebo ............ A61B 5/0075 600/318 |

FOREIGN PATENT DOCUMENTS

| WO | WO 02/076306 | 10/2002 |
| WO | WO 2017/023619 | 2/2017 |

* cited by examiner

*Primary Examiner* — Anh T Dang

(57) ABSTRACT

Some embodiments of the present invention disclose a method to reduce the intracranial cerebral blood pressure in a newborn, comprising: mounting an inflating cuff in at least one extremity of said newborn; monitoring the blood pressure in said newborn; if blood pressure rises above a predetermined value, then: inflating said inflating cuff to a predetermined level; wherein said inflating cuff further comprises blocking venous blood flow in said extremity by means of said inflating cuff and lowering cardiac output and systemic blood pressure.

19 Claims, 7 Drawing Sheets

APPARATUS AND METHOD FOR CONTROLLING SYSTEMIC BLOOD PRESSURE IN PATIENTS

FIELD AND BACKGROUND OF THE INVENTION

The present invention, in some embodiments thereof, relates to apparatus and methods for controlling systemic blood pressure in patients and, more particularly, but not exclusively, to an apparatus and methods for controlling systemic arterial blood pressure fluctuations and preventing intra-ventricular hemorrhage in patients.

Background art includes US patent application No. US20150094755A1 which discloses "a non-invasive cerebral perfusion increasing device including four cuffing pad units and a control unit which is connected to the cuffing pad units and is equipped with a blood pressure sensing module and a compression control module. In the non-invasive cerebral perfusion increasing device each cuffing pad unit respectively includes a compression pad, a compression control member and a blood pressure sensing member. The blood pressure sensing module uses the blood pressure sensing members to sense the systolic blood pressure values of the portions of each of the limbs where they are attached and the compression control module controls the degree of compression of each compression pad by controlling the compression control member to a setting desired by the user based on the sensed blood pressure value, such that the blood flow applied to the limbs is blocked and, indirectly, cerebral perfusion is increased".

International Patent Application Publication No. WO2017023619A1, which discloses "a wearable system comprises tourniquets. Each of the tourniquets comprises an inflatable chamber, and is configured to occlude blood flow in an artery of a wearer. The wearable system comprises compressed gas sources in fluid communication with the inflatable chamber of the tourniquets. The wearable system comprises valves. Each of the valves comprises an input in fluid communication with one of the compressed gas sources, and an output in fluid communication with the inflatable chamber of one of the tourniquets. The wearable system comprises fixed pressure regulators. Each of the fixed pressure regulators is in fluid communication with the valves, and is configured to regulate a pressure of the compressed gases delivered to the inflatable chamber of at least one of the tourniquets. The wearable system comprises switches. Each of the switches is configured to operate one of the valves".

International Patent Application Publication No. WO02076306A1, which discloses "a system for delivering external compression in order to stimulate angiogenesis or promote wound healing is provided. External compression causes changes in hemodynamic forces (e.g. shear stress) in the vasculature that are sensed by endothelial cells and smooth muscle cells. The stimulated cells respond by secreting various angiogenic factors and growth factors such as platelet-derived growth factors A and B and basic fibroblast growth factor. The inventive method may be used to treat patient suffering from diseases characterized by low blood flow such as peripheral vascular disease and coronary artery disease. An apparatus for delivering external compression to induce angiogenesis or promote wound healing is also provided". It involves placing inflatable cuffs on the low half of a patient's body and pressurizing and depressurizing the cuffs out-of-phase with the left ventricle.

US patent application No. US20040147956A1, which discloses "a system and method of controlling the pressure within a pressure cuff of a surgical tourniquet so as selectively to occlude blood flow within a portion of a limb of a patient, wherein a sensor determines when flow past the tourniquet is occurring so that corrective action may be taken, such as by increasing the pressure in the tourniquet or by notifying an operator of the flow past the tourniquet. The present invention may use an acoustic sensor to detect Korotkoff sounds indicating incipient blood flow past the tourniquet. When such signals are detected, the tourniquet controller may either incrementally increase the pressure in the tourniquet, or if a threshold would be exceeded by such an increase, signal an alarm indicative of the blood flow".

US patent application No. US20090287069A1, which discloses "methods for ischemic conditioning treatments of a chronic medical condition are provided. Baseline disease-related parameters of a patient with a chronic medical condition are measured. Ischemia is induced in the patient by occluding and releasing arterial flow in one or more extremities of the patient. Post-ischemia parameters in the patient are measured. The baseline and post-ischemia parameters are compared to provide an assessment of an ischemic conditioning treatment of a chronic medical condition. The repeated, scheduled delivery of ischemic conditioning provides a beneficial, therapeutic effect on the chronic medical condition. Also provided is a device for pulse oximetry during periods of absent or low pulsatile blood flow including an artificial pulse generator as well as the use of said device in assessment of ischemic conditioning".

US patent application No. US20150265286A1, which discloses: "DNA damage commonly results from exposure to diagnostic and therapeutic use of ionizing radiation, chemotoxic agents, smoking, diet and even from sedentary lifestyle. It is also a function of aging. Unrepaired DNA damage may result in accelerated aging and various forms of cancers. The invention discloses a method to harness the innate power of repetitive transient ischemia and reperfusion for protecting organs against imminent DNA damage, prevent senescence (aging) and for boosting DNA repair. This method of optimal remote ischemic preconditioning (ORIP) comprises of utilizing a pair of programmable pneumatic cuffs that inflate/deflate alternately occluding blood circulation to each of the limbs for pre-defined time intervals. ORIP can be self-administered and remotely monitored by clinician. ORIP may also be deployed as an adjunct in radiotherapy and chemotherapy for reducing the damage to normal tissue and boosting the treatment efficacy. The apparatus delivers maximal ORIP dose in shortest possible time."

US patent application No. US20140024986A1, which discloses "a limb compression device to which a cuff unit wound around a limb of a patient is connected controls compression and release of the limb by controlling air supply and exhaust of the cuff unit to repeat an compression period and a reperfusion period a predetermined number of times. At the start of the compression period, pressurization using the cuff unit is performed up to a compression pressure value based on a systolic blood pressure of the patient measured by detection of pulsation. During the compression period, the device repeats depressurization of the cuff unit at a low rate until pulsation is detected and pressurization of the cuff unit after the depressurization so as to eliminate pulsation".

U.S. Pat. No. 5,103,828, which discloses "a therapeutic system provides a clinician with an appropriate course of treatment for a patient whose cardiovascular system is operating outside the normal range of values for the left cardiac work index (LCWI) and the systemic vascular resistance index (SVRI). The left cardiac work index and the systemic vascular resistance index are calculated from the cardiac index (CI) and mean arterial blood pressure (MAP) and are displayed as relative values so that the clinician can readily determine which of the vascular parameters are outside the normal range. Preferably, the cardiac index and the other cardiac parameters are measured by an electrical bio impedance monitor that provides continuous dynamic measurement of the parameters. The left cardiac work index and the systemic vascular resistance index are calculated by a personal computer that displays the calculated parameters in an easily discernible manner".

US patent application No. US20040111006A1, which discloses "a blood pressure control system regulates blood pressure of a patient. The system includes a pressure sensor that senses blood pressure of a patient, a processor that determines if the blood pressure sensed by the pressure sensor is above a target pressure, and a blood flow regulator that reduces venous return blood flow in response to the processor determining that the sensed blood pressure is above the target pattern. The system may alternatively be employed for acutely reducing blood pressure in response to detected congestive heart failure episodes".

SUMMARY OF THE INVENTION

Some embodiments of the invention are illustrated by the examples below, noting that features shown in one example can be combined with features shown in another example, unless technically prohibited.

Example 1

A method of controlling blood pressure in a subject comprising temporarily blocking venous blood flow from at least one extremity of said subject.

Example 2

The method of example 1, wherein said blood pressure is systemic blood pressure.

Example 3

The method of example 1, wherein said blood pressure is cranial blood pressure.

Example 4

The method of example 1, wherein said blocking venous blood flow from at least one extremity is done by inflating at least one inflatable cuff mounted on said at least one extremity.

Example 5

The method of example 4, wherein said inflating comprises inflating said cuff to an internal cuff pressure from about 50% to about 90% of the diastolic arterial blood pressure value of the subject.

Example 6

The method of example 4, wherein said inflating comprises inflating said cuff to an internal cuff pressure from about 50% to about 90% of the systolic arterial blood pressure value of the subject.

Example 7

The method of example 4, wherein said inflating an inflatable cuff is performed in different extremities at different times.

Example 8

The method of example 1, comprising:
 a. mounting an inflating cuff in at least one extremity of said subject;
 b. monitoring the blood pressure in said subject;
 c. detecting when blood pressure rises above a predetermined value;
 d. inflating said inflating cuff to a predetermined level;
 wherein said inflating cuff further comprises blocking venous blood flow in said extremity by means of said inflating cuff.

Example 9

The method of example 8, wherein said mounting is performed before cutting an umbilical cord from said subject.

Example 10

The method of example 8, wherein said mounting is performed after cutting an umbilical cord from said subject.

Example 11

The method of example 8, further comprising: when blood pressure returns to normal values, deflate said inflating cuff.

Example 12

The method of example 8, further comprising alternating said inflating of said inflating cuff between inflating cuffs when more than one inflating cuff is used.

Example 13

The method of example 8, wherein said inflating an inflatable cuff is performed in different extremities at different times.

Example 14

The method of example 8, wherein said inflating an inflatable cuff is performed in different extremities at different durations.

Example 15

The method of example 8, wherein said inflating an inflatable cuff is performed to maintain the blood pressure at a determined level.

Example 16

The method of example 1, wherein said subject is a newborn subject.

Example 17

The method of example 1, wherein said subject is a premature newborn subject.

Example 18

A device for controlling the blood pressure in a subject, comprising:

a. at least one inflating cuff interconnected to at least one pump, said cuff adapted to be mounted on at least one extremity of said subject;

b. at least one input entry adapted to receive blood pressure information from said subject;

c. a central processing unit with a memory, said memory stores computer-executable instructions for controlling said central processing unit to cause said at least one pump to inflate said inflating cuff when at least one of said received blood pressure information exceeds a determined parameter;

wherein said executable instructions comprise inflating said at least one cuff to block venous blood flow and avoid blocking arterial blood flow.

Example 19

The device of example 18, wherein said blood pressure is systemic blood pressure.

Example 20

The device of example 18, wherein said blood pressure is cranial blood pressure.

Example 21

The device of example 18, wherein said inflating comprises inflating said cuff to an internal cuff pressure from about 50% to about 90% of the diastolic arterial blood pressure value of the subject.

Example 22

The device of example 18, wherein said inflating comprises inflating said cuff to an internal cuff pressure from about 50% to about 90% of the systolic arterial blood pressure value of the subject.

Example 23

The device of example 18, wherein said device further receives information regarding vital signs information, comprising at least one of PP, HR and O2 SAT.

Example 24

The device of example 18, wherein said device further comprises at least one emergency pressure relief valve.

Example 25

The device of example 18, further comprising a Doppler ultrasound device configured to monitor venous blood flow in said extremity.

Example 26

The device of example 18, further comprising a Doppler ultrasound device configured to show which intra-cuff pressure blocks all venous flow through the extremity.

Example 27

The device of example 18, wherein said cuff is configured to be mounted on a newborn subject.

Example 28

The device of example 18, wherein said cuff is configured to be mounted on a premature newborn subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
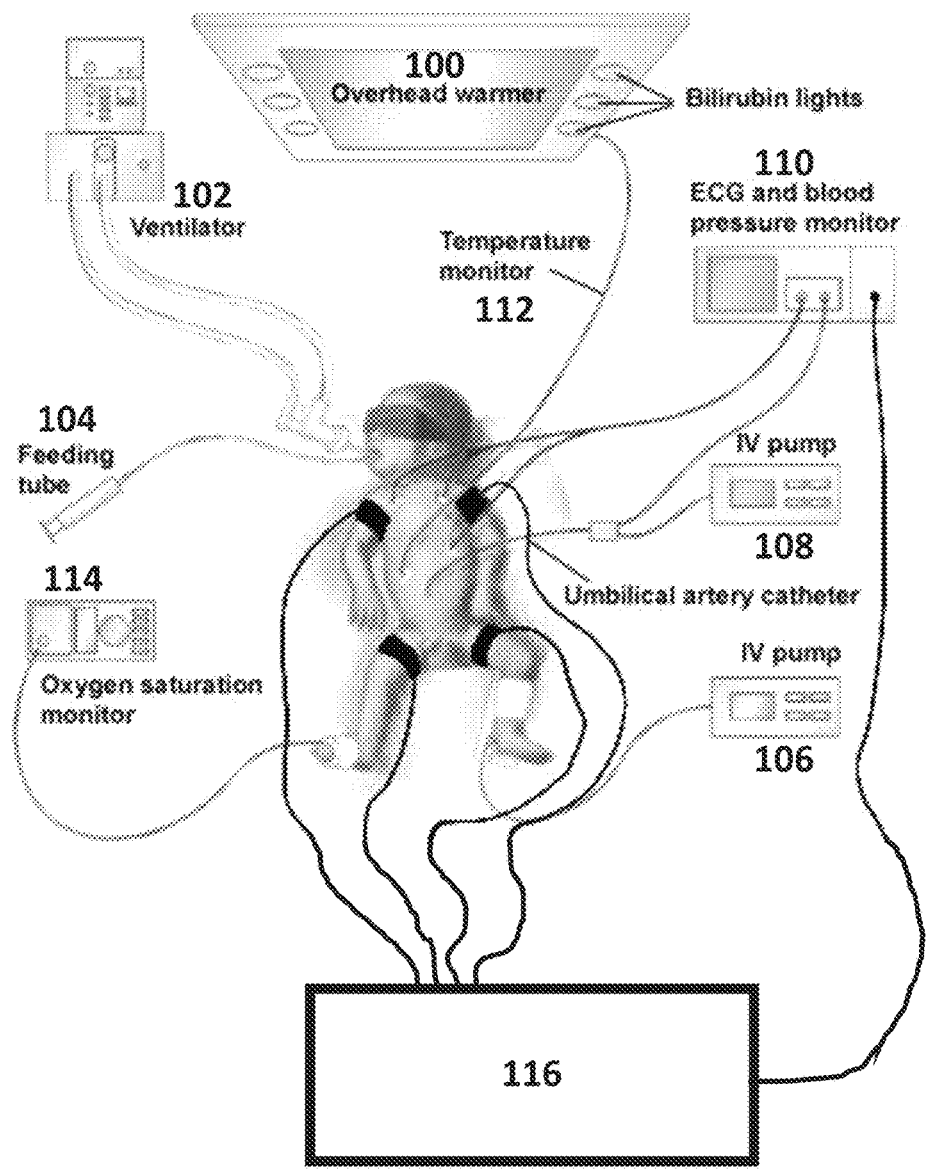
FIG. 1 is a schematic concept illustration of the device, according to some embodiments of the present invention.

The present invention, in some embodiments thereof, relates to an apparatus for controlling systemic blood pressure in patients and, more particularly, but not exclusively, to an apparatus for controlling systemic blood pressure fluctuations and preventing intra-ventricular hemorrhage in patients.

Overview

An aspect of some embodiments relates to reduction of arterial blood pressure fluctuations in subjects. In some embodiments, selectively blocking or partially blocking the flow of the venous blood in one or more extremities, leads from about 20% to about 25% reduction of the total venous blood return to the heart. Optionally, leads from about 25% to about 35% reduction of the total venous blood return to the heart. Optionally, leads from about 35% to about 45% reduction of the total venous blood return to the heart. This change leads to reduction of the cardiac output and systemic arterial blood pressure as well and thus blunting any further fluctuation of arterial systolic blood pressure and prevents fluctuations of intra-cranial systolic blood pressure and allows prevention of IVH.

It is to be emphasized that mentioning blocking of blood flow through an extremity means blocking the flow of blood in the venous vasculature but not in the arterial vasculature of the extremity. This allows avoiding ischemia of the cuffed-inflated extremity. In this regard, the above-mentioned Patents no. US20150094755A1, W2017023619A1, WO02076306A1, US200902287069A1, US20150265286A1, US20140024986A1 (underlined words), do intentionally block blood flow through arteries in the cuffed-inflated extremities, and non-intentionally, they do block the veins as well. In some embodiments, inflatable cuffs can be placed and/or inflated in at least one extremity to achieve the desired effect, which is to reduce and/or prevent increasing intracranial blood pressure.

In some embodiments, reduction of intracranial blood pressure is from about 10% to about 20%, optionally from about 20% to about 30%, optionally from about 30% to about 50%. In some embodiments, increasing blood pressure is performed by releasing the inflatable cuffs. In some embodiments, the subjects are neonatal subjects and/or newborn subjects and/or premature neonatal subjects. In some embodiments, selectively blocking or partially blocking blood flow is performed on at least one extremity of the subject. In some embodiments, blocking blood flow is performed by using inflatable cuffs attached to at least one extremity of the subject. In some embodiments, detection of abnormal blood pressure in the subject activates the cuffs. In some embodiments, detection of normal blood pressure in the subject deactivates the cuffs.

In some embodiments, the detection is performed in real-time. In some embodiments, the pressure inside the cuff is from about 5% to about 90% of the diastolic arterial blood pressure value of the subject. Optionally, the pressure inside the cuff is from about 30% to about 80% of the diastolic arterial blood pressure value of the subject. Optionally, the pressure inside the cuff is from about 40% to about 60% of the diastolic arterial blood pressure value of the subject. In some embodiments, the subjects are neonatal subjects. In some embodiments, the goal (and target settings) are selected to prevent brain damage while ensuring sufficient perfusion.

An aspect of some embodiments relates to affecting venous blood flow flowing from the extremities to the body in subjects. In some embodiments, selectively blocking or partially blocking venous blood flow flowing from the extremities to the body affects venous blood flow. In some embodiments, blocking blood flow is performed by using inflatable cuffs attached to at least one extremity of the subject. In some embodiments, detection of abnormal blood pressure in the subject activates the cuffs.

In some embodiments, detection of normal blood pressure in the subject deactivates the cuffs. In some embodiments, the detection is performed in real-time. In some embodiments, the pressure inside the cuff is from about 5% to about 90% of the diastolic arterial blood pressure value of the subject. Optionally, the pressure inside the cuff is from about 30% to about 80% of the diastolic arterial blood pressure value of the subject. Optionally, the pressure inside the cuff is from about 40% to about 60% of the diastolic arterial blood pressure value of the subject. In some embodiments, the subjects are neonatal subjects.

An aspect of some embodiments relates to reducing blood pressure in the brain of subjects by selectively blocking or partially blocking venous blood flow to the heart. In some embodiments, selectively blocking or partially blocking blood flow is performed on blood flow flowing from the extremities to the body in the subjects. In some embodiments, blocking blood flow is performed by using inflatable cuffs attached to at least one extremity of the subject. In some embodiments, detection of abnormal blood pressure in the subject activates the cuffs.

In some embodiments, detection of normal or low blood pressure in the subject deactivates the cuffs. In some embodiments, the detection is performed in real-time. In some embodiments, the pressure inside the cuff is from about 5% to about 90% of the diastolic arterial blood pressure value of the subject. Optionally, the pressure inside the cuff is from about 30% to about 80% of the diastolic arterial blood pressure value of the subject. Optionally, the pressure inside the cuff is from about 40% to about 60% of the diastolic arterial blood pressure value of the subject. In some embodiments, the subjects are neonatal subjects.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In China and USA, a total of 21,810,000 newborns are born annually. Of these infants, about 1.0% (218,100 infants) are born with a birth weight less than 1000 g, which place them in the group at risk for intraventricular hemorrhage (IVH).

IVH is a bleeding into the brain's ventricular system, where the cerebrospinal fluid is produced and circulates through the subarachnoid space. It can result from weakness of blood vessels' walls which cannot hold against significant changes in systemic and cerebral blood pressure, physical trauma or from hemorrhagic stroke.

During pregnancy, the placenta helps regulate the systemic blood pressure in the fetus. Once the fetus is born and the placenta is no longer there to assist regulate the blood pressure, the underweight newborn is at high risk to develop IVH, especially, but not only, during the first 7 days after birth.

It is a scope of some embodiments to provide devices and methods that help regulate the systemic blood pressure, cerebral arterial pressure and possibly avoid the development of IVH in subjects, and in some embodiments, also in newborn subjects.

Exemplary Device

Referring now to FIG. 1, showing a schematic concept illustration of a device of the present invention to be used specifically in newborns and/or premature newborns. Usually, premature newborns with difficulties are placed in dedicated incubators (not shown), which comprise a variety of instruments which role is to ensure the health of the new born. These incubators usually comprise an overhead warmer 100, to keep the newborn at the optimal temperature, a ventilator 102 (when needed), a feeding tube 104, one or more intravenous (IV) pumps 106-108, and a variety of instruments responsible for monitoring the vital signs of the newborn like, for example, an electrocardiogram (ECG) and blood pressure monitor 110, a temperature monitor 112 and an oxygen saturation monitor 114, just to mention a few.

In some embodiments, a device 116 for regulating the blood pressure of the newborn is added to the rest of instruments in the incubator, as shown, for example in FIG. 1. In some embodiments, the boold pressure is systemic blood pressure. In some embodiments, the blood pressure is cranial blood pressure. In some embodiments, the blood pressure is the arterial systemic and/or arterial cranial blood pressure.

Figure 2:
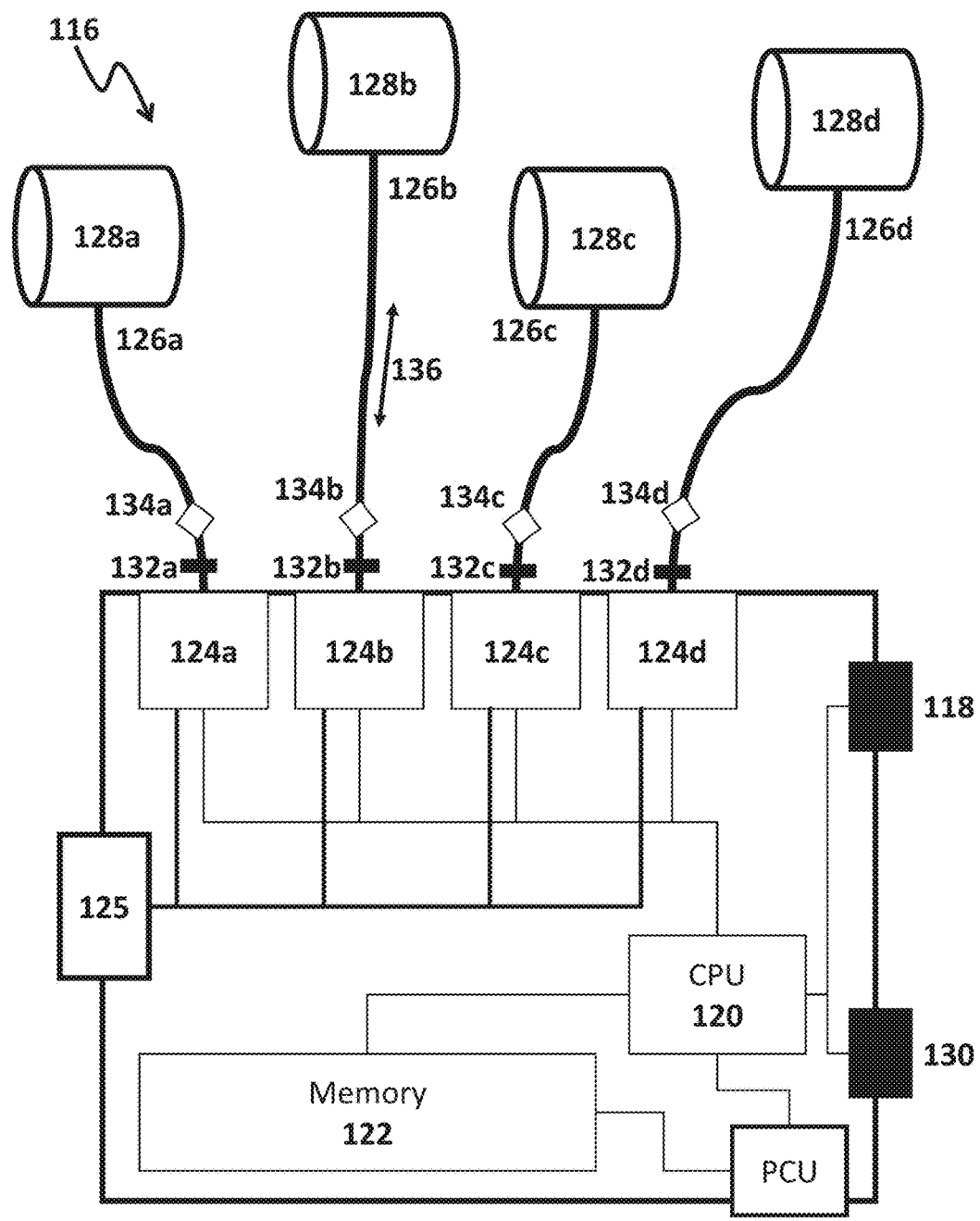
FIG. 2 is a schematic representation of the parts of the device, according to some embodiments of the present invention.

Referring now to FIG. 2, showing a schematic representation of the parts of the device 116, according to some embodiments of the present invention. In some embodiments, the device receives vital sign information from the instruments already located in the incubator or infant warmer, and especially blood pressure measurements. In some embodiments, the device includes secondary instruments which provide the vital signs of the new born. In some embodiments, vital sign instruments can be, for example, ECG, EKG, thermometer, blood pressure monitor, heartrate monitor, oxygen saturation monitor, end-tidal carbon dioxide monitor, transcutaneous Carbone dioxide monitor, and NIRS (Near-Infra-RED Spectroscopy. In some embodiments, the vital signs that are monitored are, for example, temperature, heartrate, blood pressure, oxygen saturation, end-tidal carbon dioxide monitor, transcutaneous Carbone dioxide.

In some embodiments, the device receives the vital sign information and other information via an input socket 118, which is connected to the central processing unit (CPU) 120. In some embodiments, the device comprises a memory unit 122 interconnected to the CPU 120, and capable of storing software, data, etc. In some embodiments, the CPU 120 is further connected to a series of pumps 124a-d (for example digital pumps or any other pump known in the art). In this embodiment, there are shown 4 pumps 124a-d, as a matter of example only. In some embodiments, the number of pumps is between 1 and 24. In some embodiments, each pump comprise at least one other pump for backup purposes.

In some embodiments, the device 116 comprises a gas inlet 125, which is connected to each of the pumps 124a-d so as to provide the pumps with the necessary gas when necessary. In some embodiments, the gas is air. In some embodiments, the gas is a gas other than air. In some embodiments, to each of the pumps 124a-d is connected to a proximal end of a flexible tube (126a-d), and on the distal end of each flexible tube (126a-d) there is an inflatable cuff (128a-d). In some embodiments, there are as many flexible tubes and inflatable cuffs as there are pumps. In some embodiments, the CPU 120 is programmed to control each inflatable cuff (128a-d), via said pumps (124a-d), independently to each other.

In some embodiments, each pump comprises an opening (not shown) from which air can be collected from the environment to inflate the cuffs. In some embodiments, each pump comprise a valve (not shown) at the connection with the gas inlet 125 which can be opened and closed according to the necessities of the system. In some embodiments, each pump comprise a second valve (not shown) at the connection with each flexible tube (126a-d). In some embodiments, once the inflatable cuffs are inflated to the required pressure, either of the valves can be closed so as to avoid gas from leaving the inflatable cuffs.

In some embodiments, the pumps are dual direction pumps, adapted to provide gas to the cuffs and also to remove gas from the cuffs. In some embodiments, the flexible tubes (126a-d) are used to conduct gas to the cuffs and also from the cuffs (see dualhead arrow 136). In some embodiments, the CPU 120 controls the direction of the gasflow according to the needs of the system (inflate the cuffs, deflate the cuffs).

In some embodiments, the cuffs are configured to be used on newborn subjects. In some embodiments, the cuffs are configured to be used on premature newborn subjects. Examples of cuffs for premature newborns are Neonatal One Piece Disposable Blood Pressure Cuffs by Welch Allyn® or any other similar cuffs.

In some embodiments, the device 116 comprises an outlet port 130, which can be used to connect a variety of devices like, for example, a user interface unit and/or a wireless communication unit and/or a printer and/or any peripheral device.

In some embodiments, at least one of the inflatable cuffs is mounted on at least one extremity of the newborn. In some embodiments, the extremities are the arms and/or the legs. In some embodiments, more than one inflatable cuff is mounted on the most proximal part of the extremities of the newborn.

In some embodiments, the inflatable cuff is adapted to block or partially block the venous blood flow to and/or from the extremity. In some embodiments, the inflatable cuff is adapted to block or partially block the blood flow from the extremity alone without affecting the blood flow coming from the body to the extremity. In some embodiments, the inflatable cuff is adapted to block the venous blood flow alone without affecting the arterial blood flow. In some embodiments, the arterial blood flow is not blocked and/or affected at all.

In some embodiments, real-time blood pressure measurements are used to regulate the activation of the inflatable cuff in order to block or partially block the venous blood flow.

Without being limited by a particular explanation or theory, the blood pressure is defined as the pressure of circulating blood on the walls of blood vessels. Used without further specification, "blood pressure" usually refers to the pressure in large arteries of the systemic circulation. Blood pressure is usually expressed in terms of the systolic pressure (maximum during one heart beat) over diastolic pressure (minimum in between two heart beats) and is measured in millimeters of mercury (mmHg), above the surrounding atmospheric pressure. The pressure that can block arterial blood flow is equal or higher to the systolic blood pressure. For example, in an adult having blood pressure of 120/80, arterial blood flow can be blocked by applying pressure (i.e. with an inflatable cuff) of 120 mmHg on the extremity. Similarly, the pressure that can block venous blood flow is lower or equal to the diastolic blood pressure. Therefore, in the example of the adult having blood pressure of 120/80, venous blood can be blocked by applying pressure (i.e. with an inflatable cuff) of at least 75% of the diastolic blood pressure, which is: 80*(75/100)=60 mmHg.

In some embodiments, each flexible tube (126a-d), which are connected to each inflatable cuff (128a-d), comprises a pressure measuring device (134a-d), optionally in communication with the CPU 120. Since each flexible tube is in direct communication to each respective cuff, the pressure inside the cuff will be the same as the pressure inside the flexible tube.

Each inflatable cuff (128*a-d*) has an opening immediately at its entrance where each cuff is connected to a pressure measuring device. In some embodiments, the intra-cuff pressure should not exceed 75% of the patient's diastolic blood pressure. In some embodiments, the pressure inside the cuff is from about 60% to about 75% of the diastolic arterial blood pressure value of the subject. In some embodiments, detection of venous blood flow is monitored by performing Doppler ultrasound proximal to the site where the cuff is located.

In some embodiments, each inflatable cuff (128*a-d*) comprises an emergency pressure relief valve (132*a-d*), which can be activated in cases of emergency.

In some embodiments, the device is used in newborn subjects. In some embodiments, the device is used in non-newborn subjects, for example adolescents, adults and/or elderly patients.

Exemplary Method

Figure 3:
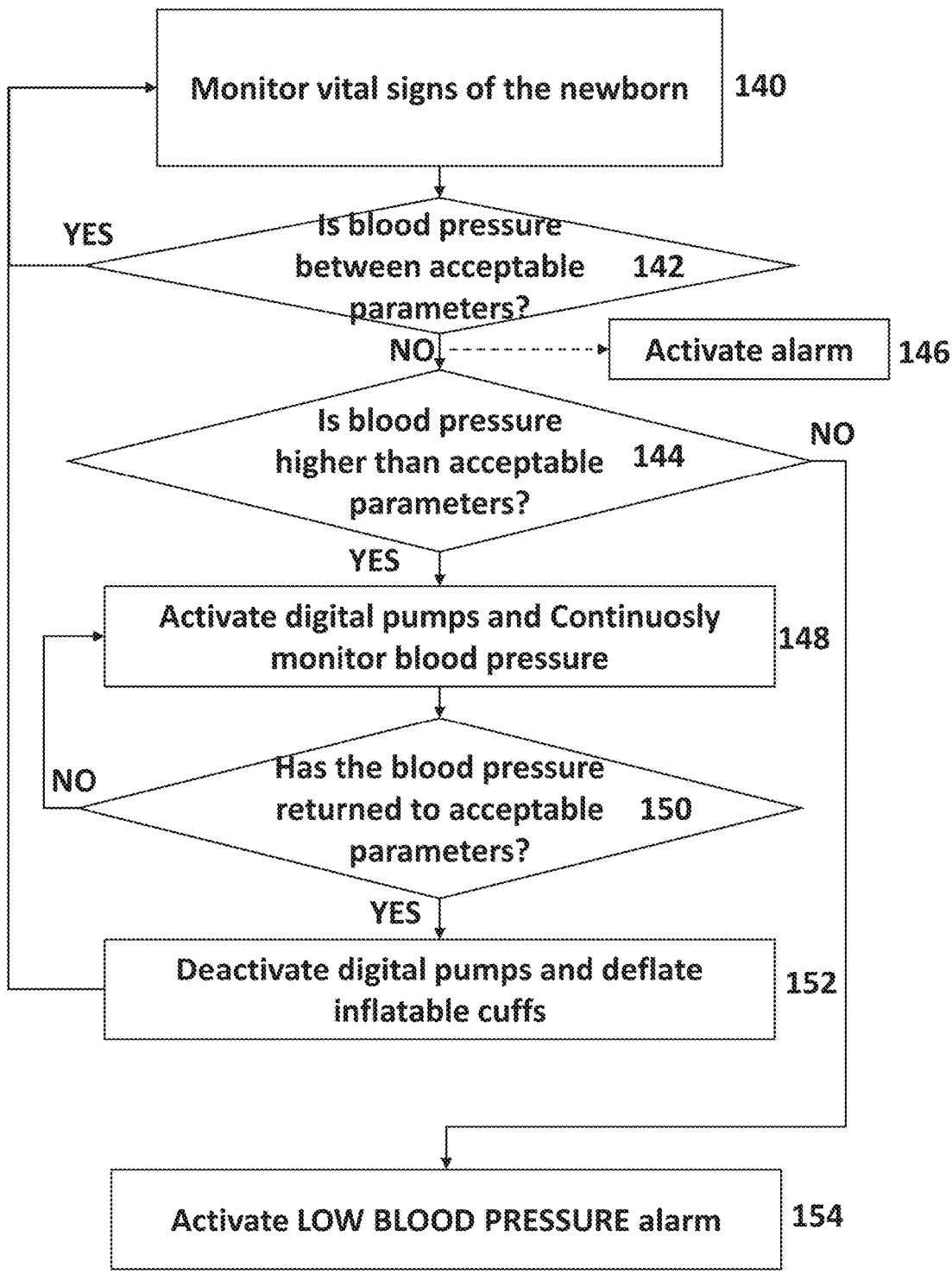
FIG. 3 is a schematic flowchart of an exemplary method, according to some embodiments of the present invention.

Referring now to FIG. 3, showing a schematic flowchart of an exemplary method of the machine. In some embodiments, the device continuously monitors the vital signs of the newborn 140. In some embodiments, the device's software subroutines monitor if the blood pressure 142 is within the predetermined acceptable parameters. In some embodiments, in case the answer is "yes" and the blood pressure is within acceptable parameters, the device continues to monitor the vital signs 140. In some embodiments, if the answer is "no", then it is assessed if the blood pressure is "higher than" the acceptable parameters 144, and an alarm is delivered to the user 146. In some embodiments, the alarm is a silent alarm since it is known that noise can affect negatively the newborn. In some embodiments, the alarm is sent to the personnel's digital devices (i.e. cellphone, tablet, beeper, etc.).

In some embodiments, if the answer is "yes", and the blood pressure is higher than the acceptable parameters, then the device activates the pumps, which inflate the inflatable cuffs and concomitantly continues to monitor the blood pressure 148. In some embodiments, it is then assessed, by the input received from the vital sign devices, if the blood pressure has returned between the acceptable parameters 150. In some embodiments, if the answer is "yes", then the device deactivates the pumps and deflates the inflatable pumps 152, and returns to monitor the vital signs of the newborn 140. In some embodiments, if the answer is "no", then the device maintains the activation of the pumps 148 until the answer is "yes". Returning to point 144 where it is assessed if the blood pressure is "higher than" the acceptable parameters, if the answer is "no", then, in some embodiments, an alarm of "low blood pressure" is activated 154.

In some embodiments, the device continues to work in order to keep the blood pressure at a stable level. In some embodiments, this is performed by activating the device intermittently and/or according to the blood pressure measurements received from the external sensors.

In general, "acceptable parameters" are set according to the specific vital signs parameters of the subject and/or the specific health status of the subject. In some embodiments, dedicated tables comprising historical statistical data on subjects are used to set the parameters of the device. In some embodiments, the parameters of the device are set manually according to the specific necessities of the subject.

Figure 4:
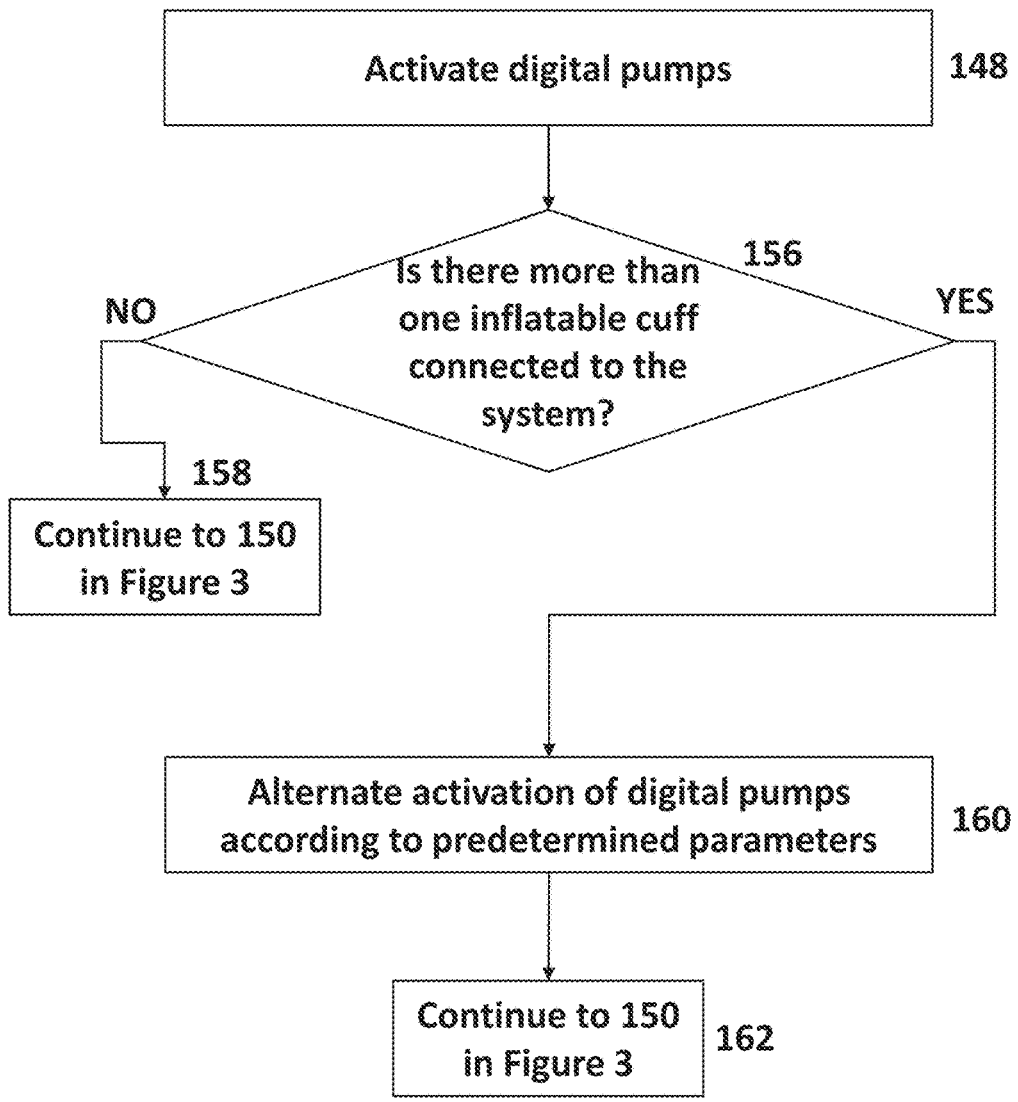
FIG. 4 is a schematic flowchart of an exemplary method of the activation of the inflatable cuffs, according to some embodiments of the present invention.

Referring now to FIG. 4, showing a schematic flowchart of an exemplary method of the activation of the inflatable cuffs. In some embodiments, when the device needs to activate the pumps 148 in order to inflate the inflatable cuffs, the system assesses if there is more than one inflatable cuff connected to the device 156. If the answer is no, then the device continues to work as shown in 150 in FIG. 3 (158). In some embodiments, when more than one inflatable cuff is used, the device alternates the activation of the different cuffs 160. Then, the device continues to work as shown in 150 in FIG. 3 (162). In some embodiments, alternation of the activation of the inflatable cuffs helps prevent physical damage to the extremity due to long term blockage of the blood flow. In some embodiments, alternation of the activation of the inflatable cuffs helps reduce the systemic blood pressure by providing multiple points of blockage of blood pressure.

Figure 5:
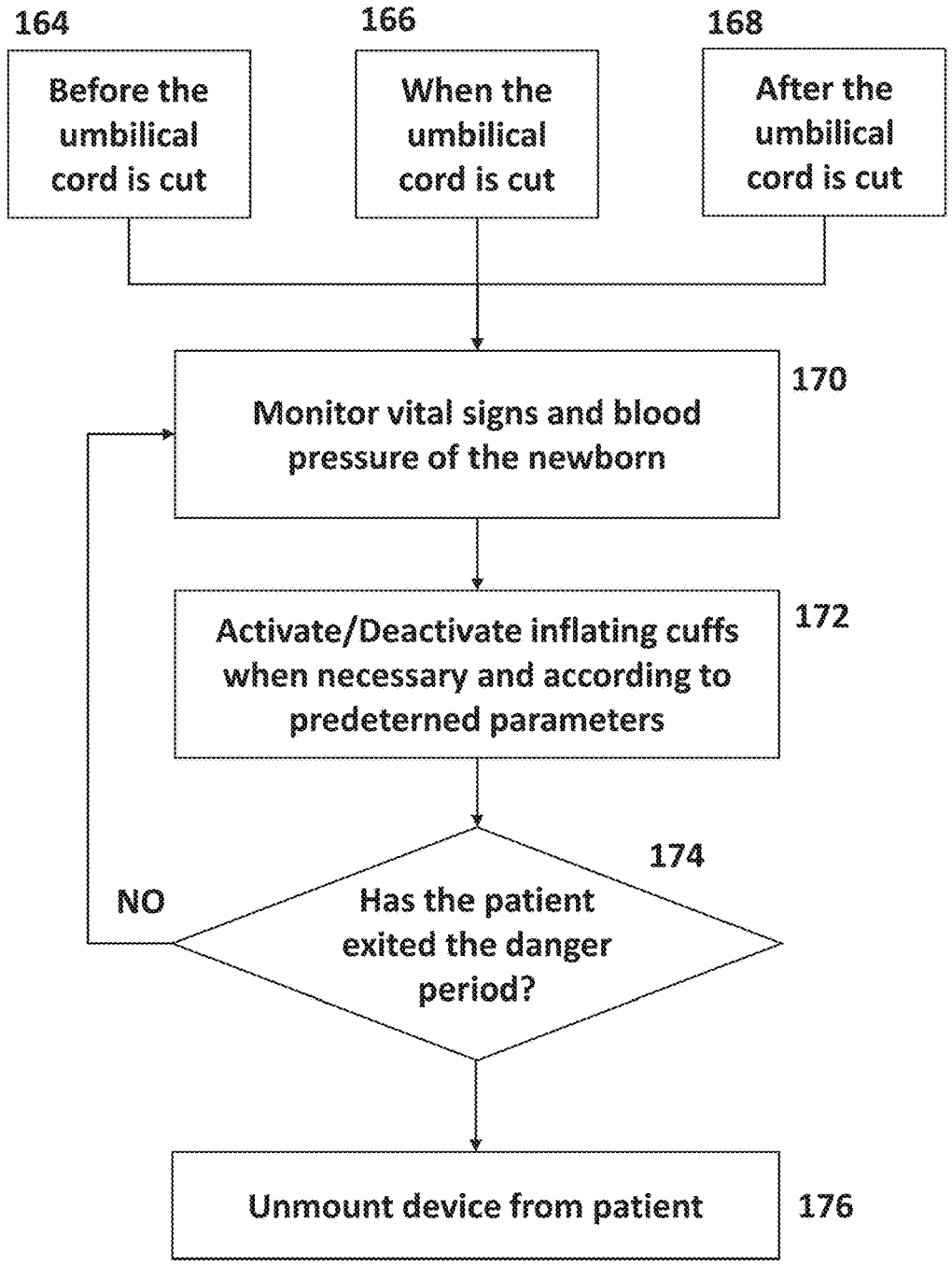
FIG. 5 is a schematic flowchart of an exemplary scenario of the use of the device, according to some embodiments of the present invention.

Referring now to FIG. 5, showing a schematic flowchart of an exemplary scenario of the use of the device, according to some embodiments of the present invention.

As mentioned above, during pregnancy, the placenta helps regulate the internal blood pressure in the fetus via the umbilical cord. Once the fetus is born and the umbilical cord is cut, the placenta can no longer assist in regulating the blood pressure. In some embodiments, the device is mounted on the newborn patient before the umbilical cord is cut 164. In some embodiments, the device is mounted on the newborn patient at the moment when the umbilical cord is cut 166. In some embodiments, the device is mounted on the newborn patient shortly after the umbilical cord is cut 168. In some embodiments, after the device is mounted on the newborn patient, the device monitors the vital signs and the blood pressure in the newborn patient 170. In some embodiments, the device operates according to the methods disclosed above 172. Without being limited by a particular explanation or theory, it is known that there is a critical period, or danger period, after the umbilical cord is cut, when the newborn patient can develop IVH.

As mentioned above this danger period can be of 7 days, but it may be longer or shorter. In some embodiments, the doctor inquires and decides when the patient has exited this danger period 174. If it is decided that the patient has not exited the danger period, then the machine stays mounted on the patient and the monitoring continues 170. If it is decided that the patient has exited the danger period, then the device can be unmounted from the patient 176. In some embodiments, stabilization of blood pressure to normal values for more than 3 days indicates that subject has exited the danger period. In some embodiments, stabilization of blood pressure to normal values from about 3 days to about 7 days indicates that subject has exited the danger period. In some embodiments, when the premature neonatal arrives at the end of what supposed to be the end of the 10 weeks of pregnancy, then it may be an indication that subject has exited the danger period.

Exemplary Combined Treatment

In some embodiments, the patient, either newborn or not, is treated using a combination of the device and methods as disclosed herein together with a pharmacological treatment. In some embodiments, the combination of the treatments provides a positive synergistic effect on the status of the patient. For example, a premature infant who is ventilated and managed by the device and also receives coagulation factor xiii to treat hemophilia, which is an abnormality that can lead to IVH.

Exemplary Use of the Device/Methods in Adults

In some embodiments, the device/methods are used on adults subjects. In some embodiments, the device/methods are used to prevent increasing and/or maintaining the intracranial blood pressure in adults subjects.

Exemplary Non-Linear Blood Pressure Dynamics

In some embodiments, blood pressure dynamics may behave in a non-linear manner in light of the use of the device and/or the methods performed by the device. In some embodiments, this non-linear behaviour is translated into a non-linear model usable in a software. In some embodiments, the software of the device further comprises methods to compress/release cuffs according to this non-linear model.

Exemplary Chronic Use of Device/Methods

In some embodiments, the device/methods are used for a long period of time. In some embodiments, the period of time is from days to weeks. For example, the device/methods can be used when there is a hypertensive crisis.

It is expected that during the life of a patent maturing from this application many relevant sensors, pumps, inflatable cuffs and vital signs monitoring devices will be developed; the scope of the term "inflatable cuffs" is intended to include all such new technologies a priori.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

In the following paragraphs, an exemplary experiment in a human subject will be disclosed.

An experiment on a 27 weeks old premature infant with RDS and umbilical artery catheter (aortic BP) was performed. Due to weak pulses and the diagnosis of aortic stenosis (coarctation of aorta) measurement of blood pressure was performed in the four extremities. Inflation of one cuff mounted in the proximal part of the leg led to a 3 mmHg decrease of systolic blood pressure: from 51 mmHg to 48 mmHg (a reduction of 5.9%), and a reduction of mean blood pressure: from 40 mmHg to 37 mmHg (reduction of 6.25%). See table below showing the results of the experiment.

|  | Systolic BP | Diastolic BP | Mean BP | Pulse Pressure | Heart rate | Location of Measurement | Limb obstructed | Cuff pressure |
|---|---|---|---|---|---|---|---|---|
| Baseline no obstruction | 51 | 31 | 40 | 20 | 132 | Descending aorta | Close to inguinal line | 102 |
| Both arterial and venous flow obstruction | 53 | 32 | 42 | 21 | 138 | Descending aorta | Close to inguinal line | 130 |
| Venous flow obstruction only | 48 | 30 | 37 | 21 | 134 | Descending aorta | Close to inguinal line | 20-30 |

Example 2

An adult volunteer (40 years old).
Inflatable cuffs were mounted on 3 limbs.
Results:
A summary of the results can be seen in the table below:

|  | TIME MIN | | | | | |
|---|---|---|---|---|---|---|
|  | 10 | 20 | 30 | 40 | 50 | 60 |
| Systolic Blood Pressure | 127 | 118 | 123 | 133 | 119 | 123 |

Figure 6:
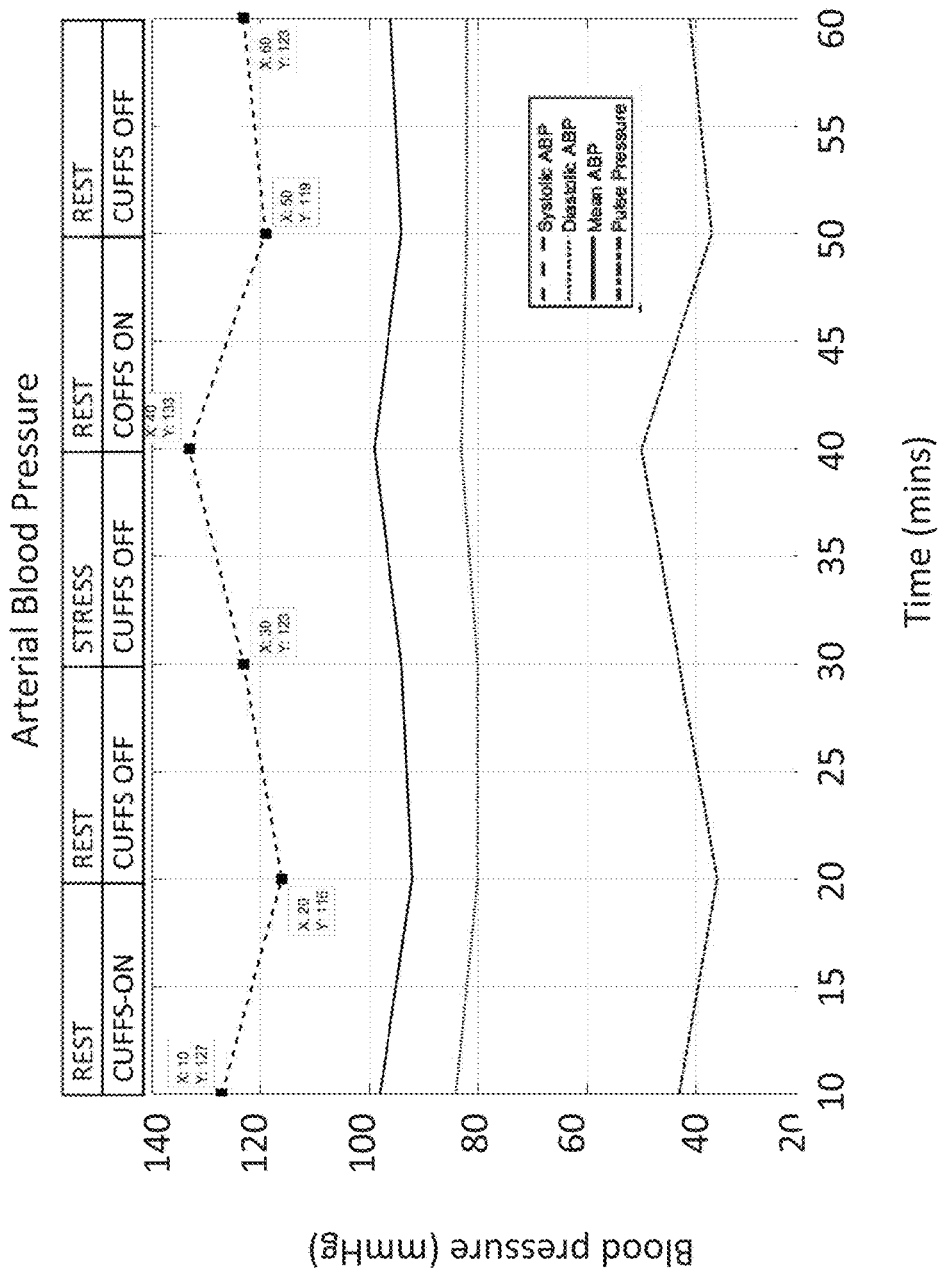
FIG. 6 is a graph showing the results of the experiment shown in example 2, according to some embodiments of the present invention.

1. Inflation of the cuffs during rest led to an (11/116) 8.6% reduction in systolic blood pressure. It is hypothesized that mounting inflatable cuffs in all 4 limbs should achieve a reduction of at least 10% in systolic blood pressure.
2. Inflation of the cuffs after physical effort led to a (14/133) 10.5% reduction in systolic blood pressure. It is hypothesized that mounting inflatable cuffs in all 4 limbs should achieve a reduction of at least 12.5% in systolic blood pressure.
See FIG. 6 for the graph showing the results of the experiment.

Example 3

Blood pressure profile in a healthy adult volunteer: Impact of venous return reduction on blood pressure fluctuations.
Volunteer Data
Age: 27 years old, weight: 85 Kilograms, height: 185 centimeters, BMI: 24.5
Experimental Protocol

| Phase | I | II | III |
|---|---|---|---|
| Time plan | 0 → 22 minutes Effect of VR obstruction on blood pressure after relax. | 23 → 45 minutes Effect of VR obstruction on blood pressure after intense exercise | 46 → 70 minutes |
| Action | Inflation of cuffs at 15 minutes | Inflation of cuffs at 35 minutes | Follow up of blood pressure, HR, O2sat and pulse pressure. |
|  | Full Inflation of cuffs within 20 seconds, 3 cuffs rotated around legs and one arm., up to a venous obstructing pressure of 65 mmHg. | | |

Figure 7:
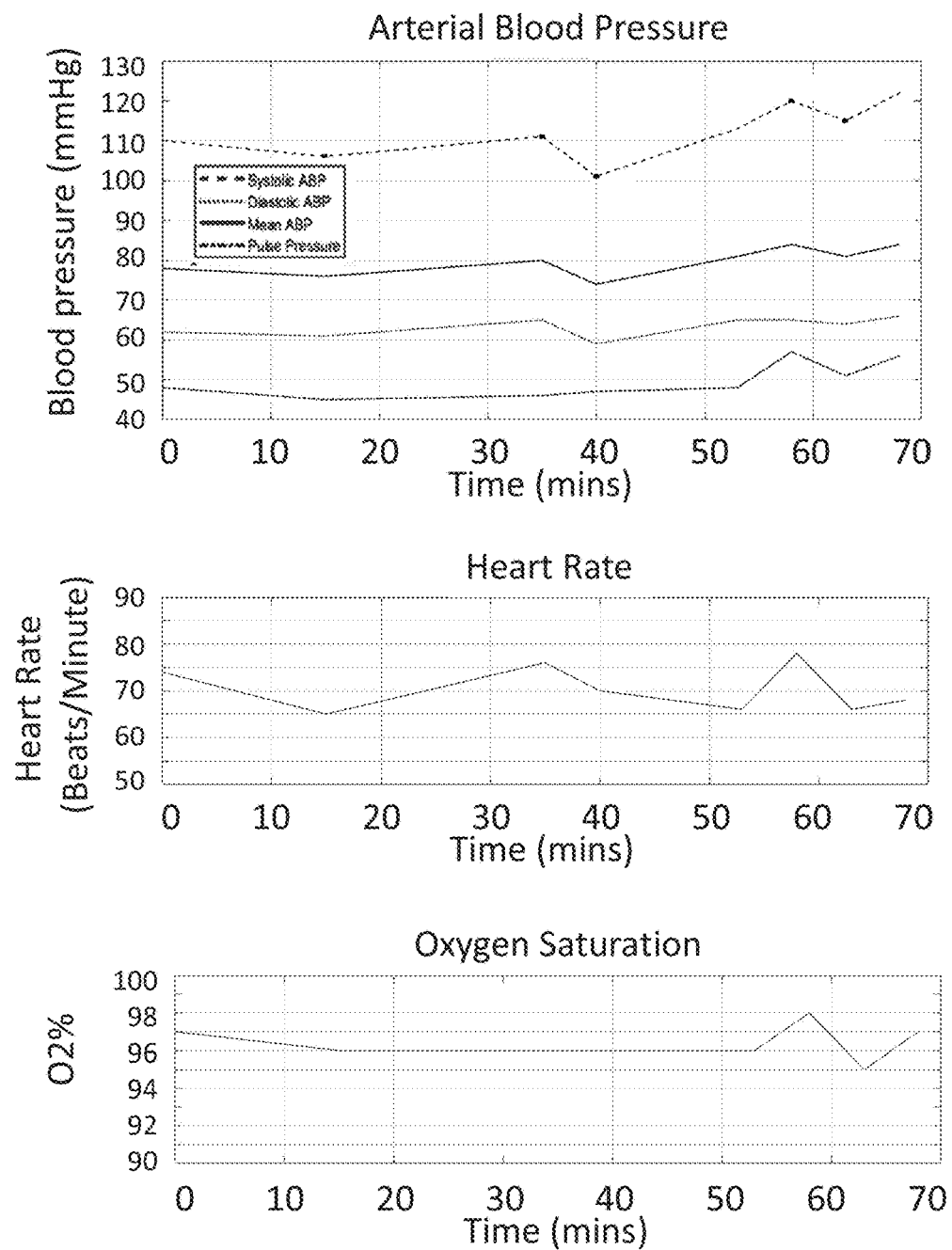
FIG. 7 are graphs showing the results of the experiment shown in example 3, according to some embodiments of the present invention.

See FIG. 7 for the graph showing the results of the experiment.

See table below

|  | When | | | | | | | |
|---|---|---|---|---|---|---|---|---|
| What | 0 | 10 | 20 | 30 | 40 | 50 | 60 | 70 |
| SYSTOLIC ABP | 113 | 106 | 111 | 101 | 113 | 124 | 115 | 122 |
| Mean BP | 78 | 76 | 80 | 74 | 81 | 84 | 81 | 84 |
| DIASTOLIC ABP | 62 | 61 | 65 | 59 | 65 | 65 | 64 | 66 |
| Pulse pressure | 48 | 45 | 46 | 47 | 48 | 57 | 51 | 56 |
| HR | 74 | 65 | 76 | 70 | 66 | 78 | 66 | 68 |
| O2 sat | 97 | 96 | 96 | 96 | 96 | 98 | 95 | 97 |

1. Inflation of the cuffs during rest led to a 7/113 (6.2%) reduction in systolic blood pressure. It is hypostasized that mounting inflatable cuffs in all 4 limbs should achieve a reduction of at least 8% in systolic blood pressure.
2. Inflation of the cuffs after physical effort led to a (9/124) 7.2% reduction in systolic blood pressure. It is hypostasized that mounting inflatable cuffs in all 4 limbs should achieve a reduction of at least 8% in systolic blood pressure.

Blocking venous blood return to the body and/or the heart by using the inflatable cuffs around the most proximal part of at least one extremity lead to reduction of systolic blood pressure even when the body was at rest (sleeping baby). Furthermore, it is expected that the device will perform better when initiated after stress to the body (infant crying, infant being touched and handled by nurses). Infants treated with the device for 20-60 seconds should present positive results, i.e. avoiding the increasing systolic blood pressure, can show compensatory rise of blood pressure after deflation of the cuffs. In some cases, it might be required to perform repetitive activation of the device.

Example 4

In the following paragraphs, an exemplary experimental protocol for a proof of concept in non-human animals will be explained.
Exemplary General Protocol for the Experiment
Type of animal: piglets that were born up to 36 hours before the experiment.
Pre-Experimental Conditions:
Anesthesia: partially or total anesthetized
Respirator: only if necessary
IV: fluids only.
Parameters Observed
    Systemic blood pressure (BP)
    Blood pressure fluctuations (any increase or decrease in mean systemic BP of 10% or more)

Pulse pressure
Breathing
Pulse
Saturation
$CO_2$ in exhaled air or subcutaneously measured
Urine
Inflation pressure of limb via manual BP apparatus and its cuffs
Cerebral blood flow via us carotids
Venous blood flow above obstruction
Which inflation pressure stops venous flow from limb
Cardiac output via Doppler US in descending abdominal aorta
Devices Used
Monitor showing BP, PP, HR, O2 SAT, transcutaneous $CO_2$ monitor. Online with alarms
Manual pressure monitors
Inflatable cuffs
Ultrasound to monitor cerebral blood flow (CBF) and the required pressure needed to complete block venous blood flow in the proximity
Central arterial catheter
Central venous catheter
Respirator
Urine catheter Experimental Procedure Phase 1: Adaptation Period (Between 20 to 30 Minutes)

During this phase the non-human subject is prepared for the experiment. All catheters and devices (Gastric, arterial central, venous central, Peripheral venous, BP via a monitor, Cuffing limbs) are mounted into the subject and connected to the device.

Phase 2: Induced Change in Blood Pressure in the Subject (Between 40 to 90 Minutes)

During this phase the change in the blood pressure is induced in the subject by reducing the dosage of anesthesia medication to a marginal dosage (near wake up state). The effect of the reduction of the anesthesia is to cause discomfort to the subject in order to increase the blood pressure. Several measurements will be performed: BP, PP, HR, O2 SAT, brain ultrasound, venous flow in the extremities.

Phase 3: Experiment

During this phase the cuffs will be inflated in order to block or partially block the venous blood flow until the blood pressure in the subject returns to normal values (similar to those measured during Phase 1).

It is hypothesized that there will be a systolic blood pressure increase of more than 10% (8-12%) that lasts for at least 30 seconds.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for controlling the blood pressure in a subject, comprising:
    a. at least one inflating cuff interconnected to at least one pump, said at least one inflating cuff adapted to be mounted on at least one extremity of said subject;
    b. at least one input entry adapted to receive blood pressure information from said subject;
    c. a central processing unit with a memory, said memory stores computer-executable instructions for controlling said central processing unit to cause said device to:
    block venous blood flow by inflating said at least one inflating cuff when at least one of said received blood pressure information exceeds a determined parameter; and
    unblock said venous blood flow by deflating said at least one inflating cuff when at least one of said received blood pressure information returns below said determined parameter;
    wherein said executable instructions comprise instructions to block said blood flow by inflating said at least one inflating cuff to block venous blood flow and avoid blocking arterial blood flow.

2. The device according to claim 1, wherein said blood pressure information comprises systemic blood pressure.

3. The device according to claim 1, wherein said blood pressure information comprises cranial blood pressure.

4. The device according to claim 1, wherein said inflating comprises inflating said at least one inflating cuff to an internal cuff pressure from about 50% to about 90% of the diastolic arterial blood pressure value of the subject.

5. The device according to claim 1, wherein said inflating comprises inflating said at least one inflating cuff to an internal cuff pressure from about 50% to about 90% of the systolic arterial blood pressure value of the subject.

6. The device according to claim 1, wherein said device further receives information regarding vital signs information, comprising at least one of PP, HR and O2 SAT.

7. The device according to claim 1, wherein said device further comprises at least one emergency pressure relief valve.

8. The device according to claim 1, further comprising a Doppler ultrasound device configured to monitor venous blood flow in said extremity.

9. The device according to claim 1, further comprising a Doppler ultrasound device configured to show at which internal cuff pressure of said at least one inflating cuff all venous flow through the extremity is blocked.

10. The device according to claim 1, wherein said at least one inflating cuff is configured to be mounted on a newborn subject.

11. The device according to claim 1, wherein said at least one inflating cuff is configured to be mounted on a premature newborn subject.

12. The device according to claim 1, wherein said device further comprises at least one backup pump.

13. The device according to claim 1, wherein said at least one inflating cuff comprises at least one valve at the connection with said at least one pump configured to be closed to prevent gas from leaving said at least one inflating cuff.

14. The device according to claim 1, wherein said at least one pump is a dual direction pump configured to provide gas to said at least one inflating cuff and to remove gas from said at least one inflating cuff.

15. The device according to claim 14, wherein said central processing unit is configured to cause said at least one pump to either deflate or inflate said at least one inflating cuff.

16. The device according to claim 1, wherein said device further comprises at least one outlet port configured to connect external devices to said device.

17. The device according to claim 1, wherein said at least one inflating cuff is sized to be mounted on a non-newborn subject.

18. The device according to claim 1, wherein said computer-executable instructions for controlling said central processing unit are configured to follow a linear model of blood pressure dynamics.

19. The device according to claim 1, wherein said computer-executable instructions for controlling said central processing unit are configured to follow a non-linear model of blood pressure dynamics.

* * * * *